United States Patent
Li et al.

(10) Patent No.: US 9,750,430 B2
(45) Date of Patent: *Sep. 5, 2017

(54) METHODS OF INTRAVENOUS DRUG MONITORING

(75) Inventors: Bo Li, Rexford, NY (US); Rui Chen, Clifton Park, NY (US); Xuefeng Wang, Schenectady, NY (US); Hanna Elina Viertio-Oja, Espoo (FI)

(73) Assignee: General Electric Company, Niskayuna, NY (US)

( * ) Notice: Subject to any disclaimer, the term of this patent is extended or adjusted under 35 U.S.C. 154(b) by 617 days.

This patent is subject to a terminal disclaimer.

(21) Appl. No.: 13/173,809

(22) Filed: Jun. 30, 2011

(65) Prior Publication Data

US 2012/0277613 A1 Nov. 1, 2012

Related U.S. Application Data

(60) Provisional application No. 61/479,419, filed on Apr. 27, 2011.

(51) Int. Cl.
| | |
|---|---|
| *A61B 5/08* | (2006.01) |
| *A61B 5/00* | (2006.01) |
| *A61M 16/10* | (2006.01) |
| *A61M 16/06* | (2006.01) |

(52) U.S. Cl.
CPC ............ *A61B 5/082* (2013.01); *A61B 5/0816* (2013.01); *A61B 5/4848* (2013.01); *A61M 16/06* (2013.01); *A61M 16/104* (2013.01); *A61M 2016/1035* (2013.01); *A61M 2202/0241* (2013.01)

(58) Field of Classification Search
CPC ................ A61M 16/06; A61M 16/104; A61M 2016/1035; A61M 2202/0241; A61M 2230/437; A61B 5/082

USPC ...... 128/203.12, 203.14, 204.22; 604/19, 24, 604/66, 67

See application file for complete search history.

(56) References Cited

U.S. PATENT DOCUMENTS

| | | | |
|---|---|---|---|
| 6,631,291 | B2 | 10/2003 | Viertio-Oja et al. |
| 6,658,396 | B1 | 12/2003 | Tang et al. |
| 6,981,947 | B2 | 1/2006 | Melker |
| 7,104,963 | B2 | 9/2006 | Melker et al. |
| RE41,291 | E | 4/2010 | Viertio-Oja et al. |
| 7,774,052 | B2 | 8/2010 | Burton et al. |

(Continued)

OTHER PUBLICATIONS

Chen et al. ("Linear and Nonlinear Quantification of Respiratory Sinus Arrhythmia during Propofol General Anesthesia". 31st Annual International Conference of the IEEE EMBS, Minneapolis, Minnesota, USA, Sep. 2-6, 2009).*

(Continued)

*Primary Examiner* — Jacqueline Cheng
*Assistant Examiner* — Puya Agahi
(74) *Attorney, Agent, or Firm* — Pabitra K. Chakrabarti

(57) ABSTRACT

A method of monitoring a concentration of an anesthetic drug using a patient's breath is provided. The method comprises forming a breath sample using the patient's breath; exposing one or more sensors to the breath sample; detecting one or more components of the anesthetic drug in the breath sample; measuring a concentration of at least one of the components of the anesthetic drug in the breath sample; and determining a concentration of the component in a plasma of the patient using a transfer function and the concentration of the component in the breath sample.

16 Claims, 2 Drawing Sheets

(56) References Cited

U.S. PATENT DOCUMENTS

| | | |
|---|---|---|
| 7,899,525 B2 | 3/2011 | John et al. |
| 2007/0203448 A1* | 8/2007 | Melker et al. .................. 604/24 |
| 2008/0011294 A1* | 1/2008 | Heesch ............. A61M 16/0051 |
| | | 128/200.24 |
| 2010/0305499 A1 | 12/2010 | Matsiev et al. |

OTHER PUBLICATIONS

Jenkins et al., Effects of Temperature and Volatile Anesthetics on GABAA Receptors, Anesthesiology, v.90, No. 2, Feb. 1999, p. 481-491.*

Wang et al., Modeling of a Gas Concentration Measurement System, Engineering in Medicine and Biological Society, IEEE-EMBS, 2005.*

Shabnam Noor and Saida Hossain; "Development of an Audio Evoked Response System to Facilitate Anaesthesia Monitoring"; 50Pages.

Simanski et al; "Progress of automatic drug delivery in anaesthesia—The 'Rostock assistant system for anaesthesia control (RAN)'"; International Journal of Adaptive Control and Signal Processing Int. J. Adapt. Control Signal Process. 2009; 23:504-521; Published online Sep. 17, 2008 in Wiley InterScience (www.interscience.wiley.com). DOI: 10.1002/acs.1068; 18Pages.

* cited by examiner

METHODS OF INTRAVENOUS DRUG MONITORING

This non-provisional application claims the benefit of priority under 35 U.S.C. §119(e) to U.S. Provisional Patent Application Ser. No. 61/479,419, filed Apr. 27, 2011, which is herein incorporated in its entirety by reference.

TECHNICAL FIELD

The invention relates generally to intravenous drug monitoring, and more specifically to intravenous anesthesia drug monitoring.

BACKGROUND

Intravenous anesthetic agents are typically short acting agents. The intravenous anesthetic agents are generally used in induction and maintenance phase of anesthesia. Based on the rapid distribution and metabolism of the anesthetic agents in patients' bodies, the anesthetic must be re-dosed frequently to ensure the anesthesia depth and the success of surgery. The control of the anesthesia amount is mainly based on the prediction of pharmacokinetic models. However, the pharmacokinetic models are not able to compensate the individual difference of each patient's physical characteristics, and may lead to determine a dose which may be an under-dose or overdose for the patient, either resulting in early wakeup during procedure or causing side effects. Therefore, precise and real-time detection of anesthetic concentration in plasma is greatly needed to improve the quality of anesthesia monitoring.

Different approaches are available to monitor patients under anesthesia procedures. These methods can be categorized into direct measurement of anesthetic drug concentration in blood and indirect measurement by monitoring a patient's conscious level, in addition to normal physiological parameters such as oxygen saturation, blood pressure, or heart rate. The anesthetic drugs may be detected in plasma or breath samples. Monitoring of anesthetic drug concentration in plasma or breath may provide better protection to patients than other conventional methods. The depth of anesthesia for a known concentration of drug in plasma is less variable; however, there is a significant interpatient variability in the drug concentration in plasma achieved with a known dose of anesthetic drug. The direct measurement of drug in plasma is invasive, time consuming and expensive. In contrast to direct method, an indirect breath based approach would be non-invasive, and provide continuous monitoring, faster response times and lower costs.

Therefore, the methods of monitoring a plasma concentration of intravenously delivered anesthetic drug by measuring the drug vapor concentration from exhaled breath are highly desirable.

BRIEF DESCRIPTION OF THE INVENTION

In one example, a method of monitoring a concentration of an anesthetic drug using a patient's breath comprises forming a breath sample using the patient's breath, exposing one or more sensors to the breath sample, detecting one or more components of the anesthetic drug in the breath sample, measuring a concentration of at least one of the components of the anesthetic drug in the breath sample, and determining a concentration of the component in a plasma of the patient using a transfer function and the concentration of the component in the breath sample.

In one example, the method of monitoring a propofol concentration in plasma comprises, forming a breath sample using a patient's breath, exposing one or more sensors to the breath sample, detecting the propofol in the breath sample, measuring a concentration of propofol in the breath sample, and determining a concentration of the propofol in a plasma of the patient using a transfer function and the concentration of the propofol in the breath sample.

BRIEF DESCRIPTION OF THE DRAWINGS

These and other features of embodiments of the invention will be more readily understood from the following detailed description of the various aspects of the invention taken in conjunction with the accompanying drawings that depict various embodiments of the invention, in which.

DETAILED DESCRIPTION OF THE INVENTION

Figure 1:
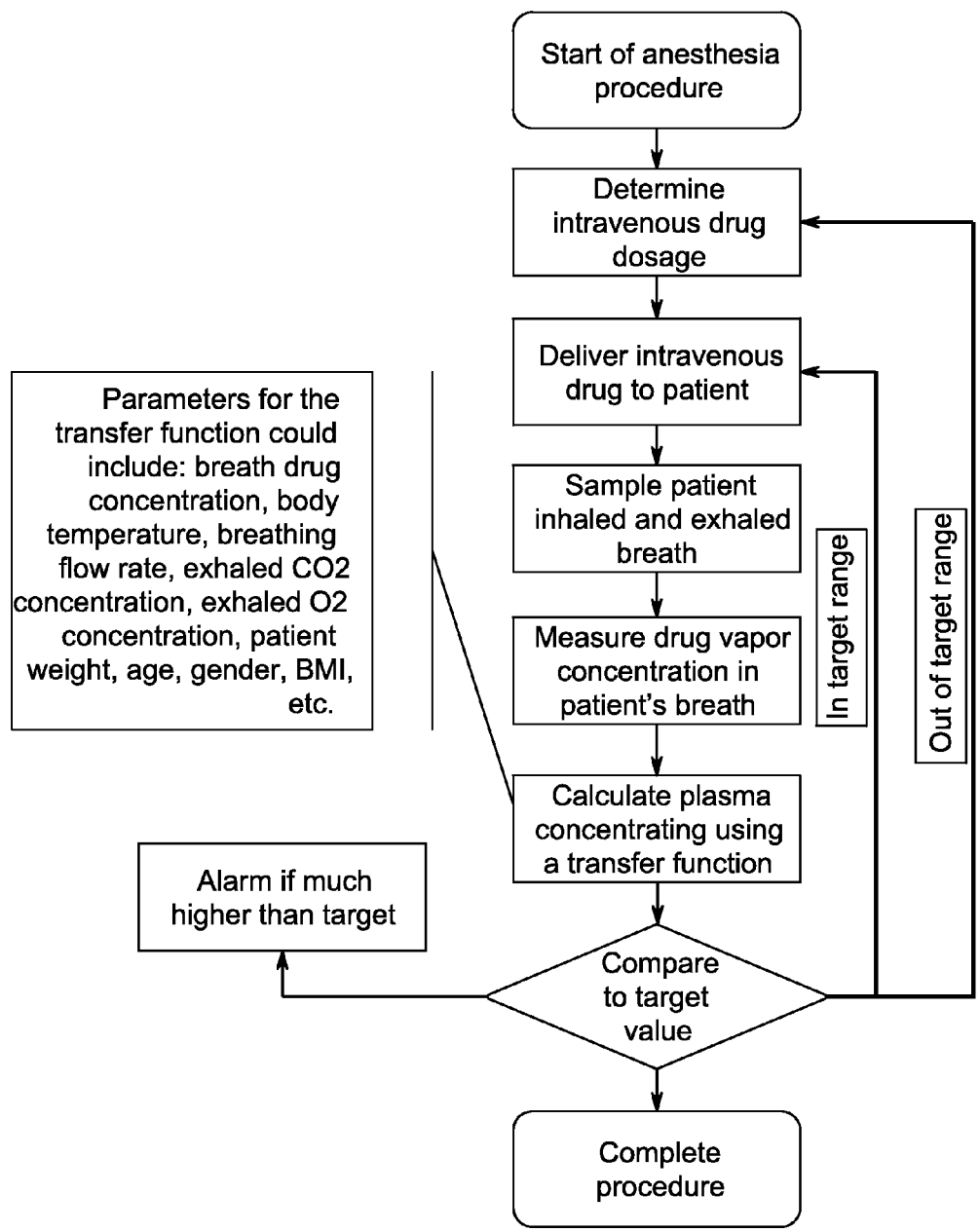
FIG. 1 is a schematic flow diagram of an illustrative method for intravenous anesthetic drug monitoring according to one aspect of the invention.

One or more examples of a method are adopted for detecting a concentration of an anesthetic drug in plasma during general or total intravenous anesthesia operations. Anesthetic drugs may be administered parenterally, sublingually, transdermally, by intravenous bolus, and by continuous infusion. Anesthetic agents may be administered in an amount for analgesia, conscious sedation, or unconsciousness as per its known dose. The concentration of the anesthetic agent in exhaled breath reflects the condition of a patient under the anesthetic drug treatment. For example, higher concentration of drug in blood stream provides information on accumulation of drugs in the blood stream, which may cause a deep level of anesthesia. In another example, if the concentration of anesthetic drug in the blood stream decreases more rapidly with time, this may possibly lead to inadequate anesthesia and premature emergence.

One example of the method of monitoring a concentration of an anesthetic drug using a patient's breath, comprises forming a breath sample using the patient's breath, exposing one or more sensors to the breath sample, detecting one or more components of the anesthetic drug in the breath sample, measuring a concentration of at least one of the components of the anesthetic drug in the breath sample, and determining a concentration of the component in a plasma of the patient using a transfer function and the concentration of the component in the breath sample.

In another example, the method is adapted to monitor the concentration of anesthetic drug in plasma, wherein the drug is administered intravenously. The intravenously delivered anesthetic drug concentration in plasma is monitored by measuring the drug vapor concentration in a patient's breath. For the intravenous anesthetics application, the quantity of drug required should include a sufficient depth of anesthesia without accumulating an excessive amount of anesthetic drug.

In accordance with one or more examples of the method, the anesthetic drug is directly administered into a patient's blood stream, rather than administering through a breathing circuit. In some examples, the administered anesthetic drug is bound to proteins or absorbed into fat, and the bound or absorbed drug does not produce a pharmacological effect. In one or more examples, a portion of the bound drug may exist in equilibrium with an unbound drug. In some examples, the drug may exist in a free form. Drug metabolism typically precedes clearance of the drug from the bloodstream and termination of its effect. The effect of the drug may also be terminated by the excretion of the free drug in the urine, digestive tract or in exhaled breath. The concentration of an anesthetic agent in the body depends on the amount of anesthetic agent administered and the amount of the agent eliminated from the body over a given period of time. The concentration indicates a characteristic of metabolism of the agent in the patient's body.

The intravenously delivered drug may be selected from but is not limited to, an analgesic drug, an amnesia drug, a muscle relaxation drug or a chemotherapeutic drug. An example of an anesthetic drug is propofol, which is widely used as a short acting intravenous anesthetic agent, hydrophobic and volatile in nature. The propofol is administered as a constant intravenous infusion to deliver and maintain a specific plasma concentration. The clearance of propofol from the body is controlled by metabolic processes, primarily through the liver.

For monitoring concentration of anesthetic drug in a breath sample, collection of a breath from a patient is the initial step. In one or more examples of the method, the patient's breath is collected from an inhaled breath, an exhaled breath, or a combination of the two. The exhaled breath comprises various types of breath or gases depending on the sequence in which it comes out. At the beginning of exhalation, the breath coming out from the mouth and upper respiratory tracts (anatomically inactive part) of the respiratory system called "dead space". This is followed by a plateau stage, wherein during an early part of the plateau stage, the breath comprises a mixture of dead space and metabolically active gases. The last portion of the exhaled breath comprises an end-tidal gas, which comes from the alveoli. In one example, the exhaled breath sample is collected at end-tidal breathing. Single or multiple samples may be collected for detecting anesthetic drugs. The breath sample may also comprise inspiratory gases. Inspiratory gases are the gases that patient inhaled during operation. The inspiratory gases may comprise synthesized air, or anesthesia gases. In some embodiments, the breath sample comprises end-tidal gas, gas from dead-space, inspiratory gas, or combinations thereof. In one embodiment, the breath sample comprises a mixed gas which may be a combination of end-tidal gas, gas from dead-space, and inspiratory gas.

The patient's breath is collected using a breathing circuit, a flow channel, a flow tubing, or an adapter. The breathing circuit is used to take a breath sample from the patient who is administered one or more drugs intravenously. In some embodiments, the breathing circuit may be directly connected to the patient's mouth or nose. In this embodiment, the circuit is called a mainstream breathing circuit. In a different embodiment, the breathing circuit may be connected to a separate tube, which is directly connected to the patient's mouth or nose, otherwise referred to as a side stream configuration. In some embodiments, a flow channel or tubing may be attached to, for example, a mouthpiece or nosepiece. The mouthpiece or nosepiece may be used to readily transmit the exhaled breath to the sensor. In another example, exhaled breath is collected through an adapter at the proximal end of the respiratory track and drawn or pushed through a tubing to the sensor.

The material for making a breathing circuit, flow channel, tubing or adapter may be selected depending on the surface property of the material. As many of the components of anesthetic drug may be sticky in nature, the material of the breathing circuit, tubing, flow channel or adapter is desirable to have non-sticky nature. For example, one of the intravenous drugs is Propofol, which is a sticky molecule and tends to stick to the surface of the breathing circuit, flow channel, tubing or adapter. The materials of the breathing circuit, flow channel, tubing or adapter may include, but are not limited to Teflon, stainless steel, or glass. In some examples, the breathing circuit, flow channel, tubing or adapter may be coated with non-sticking material. In some examples, heated breathing circuit, flow channel, tubing or adapter may also be used to reduce surface sticking of various components of anesthetic drugs, such as propofol.

Depending on the sample size and detector response time, the breath samples may be collected on successive cycles. The collection of breath from patient may be a continuous process or an intermittent process. The collection of sample is immediately followed by sampling process to determine concentration of the anesthetic drugs, while the patient is under general or total intravenous anesthesia operation.

The collected breath from the patient is processed to improve the measurement accuracy and to introduce to sensors for measuring concentration of anesthetic drug in the breath sample. The "forming of breath sample" is achieved by processing of the collected breath employing various processing techniques which result "breath sample". The method comprises sampling of a patient's inhaled breath, exhaled breath, or combinations thereof. The processing of the patient's breath may comprise filtration, differential permeation, concentration, dilution, desiccation, controlling of the breath pressure, controlling of the breath temperature, controlling of breath humidity, controlling of breath flow rate, normalizing the vapor density of the breath, or combinations thereof. In one example of the method, the forming of the breath sample comprises use of two or more of filtration, breath pressure control, breath temperature control, breath humidity control, breath flow rate control, or vapor density normalizing techniques. For example, the filters are used to remove or reduce unwanted substances in the breath sample, such as water vapor, sputum, food particles, or interfering compounds that may lower the sensitivity and selectivity of the sensors used to detect target drug compounds. Membranes or hollow fibers, such as PDMS membrane or PDMS hollow fibers may be used to separate interfering compounds based on their permeation differential. The pressure sensor monitors the breathing pressure of the breath flow and one or more pressure controllers may control the pressure of the breath flow to provide required pressure while exposing to system electronics to detect breathing patterns of the patient or provide calibration data. The breath sample may also be mixed or diluted with a known carrier gas to achieve desired pressure or flow rate. The temperature sensor monitors the temperature of the breath sample, and a temperature controller controls the temperature of the breath sample and expose it to the system electronics for detecting breathing patterns of the patient and/or provides data calibration or correction. In one example, the exhaled breath is allowed to dry before being exposed to a sensor, and the vapor density of each sample of exhaled breath may be normalized before the sensing procedure. One or more flow sensors may detect the breathing flow rate of the patient. One or more water traps may be used to store water condensates from the breath sample.

The processing of the patient's breath is performed periodically or continuously. In one embodiment, for sampling end-tidal gases, samples may be collected throughout the exhalation phase of respiration. In another embodiment, breath samples are collected at the distal end of the endotracheal tube through a tube with a separate sampling port. This may improve sampling by allowing a larger sample to be collected during each respiratory cycle.

An example at the method comprises using one or more of the sensors for detecting anesthetic drugs in breath sample. The sensors are exposed to the breath sample for detecting the presence of one or more of the components of the anesthetic drug. With in-line sampling, the sensor may be placed proximal to the respiratory track directly in the breath stream. One or more of the non-limiting examples of sensors exposed to the breath sample are flow sensors, pressure sensors, temperature sensors, gas sensors, humidity sensors, chemical sensors, or intravenous drug sensors. For example, the flow sensor may be used to detect flow rate of the sample at the starting and completion of exhalation process. More specifically, the possible sensors may include, but are not limited to, ion mobility spectrometer, differential mobility spectrometer, photoionization detector, infrared absorption spectrometer, photoacoustic spectrometer, electrochemical sensors, gravimetric sensors, thermal conductivity sensors, mass spectrometer, or gas chromatography system. For example, electrochemical detection is employed for the quantification of propofol after chromatographic separations. Propofol is detectable for its oxidation of phenol structure. Furthermore, increasing pH may significantly lower the oxidation potential of propofol. The lower working potential may decrease background signal significantly, since interferences in breath have higher oxidation potentials which may not go down with pH as propofol does, therefore they are not detectable at the low working potential.

The humidity in the exhaled breath causes problems for detecting various components of the breath sample. When using humidity sensitive devices, the method may employ an electronic nose technology so that a patient can exhale directly into the device with a means to dehumidify the sample. This may be accomplished using a commercial dehumidifier or a heat moisture exchanger to prevent desiccation of the airway during ventilation with dry gases. In some examples, the patients may simply exhale breath through their nose which is an anatomical, physiological dehumidifier for normal respiration. In some examples of the methods, the breath sample is routed through the preconcentrator before being passed over the sensor array. By heating and volatilizing the breath (or gases), humidity may be removed. The sensor may be used to identify a baseline spectrum for the patient prior to delivery. This is beneficial for detecting more than one drug if the patient receives more than one drug at a time and detecting possible interference from different foods and odors in the stomach, mouth, esophagus and lungs.

In one or more examples of the method, the intravenous drug sensor used for measuring concentration of the drug in the breath sample may be a gas sensor or a vapor sensor depending on the drug being monitored. In some examples, the intravenous drug sensor measures the concentration of one or more drugs in the breath sample. In one or more embodiments, the gas sensors are selected from carbon dioxide ($CO_2$) sensors, oxygen ($O_2$) sensors, or drug vapor sensors, or combinations thereof. In some embodiments, the gas sensors detect $CO_2$ and $O_2$ concentration from the breath sample. $CO_2$ concentration is an important parameter for breath measurement. It may be used to detect the end tidal volume of the breath. The end tidal breath is often considered as the most significant part of the entire exhaled breath for analysis. As the end tidal breath typically passes through the gas exchange process in lung and comprises highest $CO_2$ concentration, a detection of the end tidal breath using a $CO_2$ sensor is easier. In a normal human subject, this concentration is in a range from about 4% to 5%. Early portions of the breath may contain gas in the dead volume of the air way, which does not participate in the gas exchange in lung. This part of the breath typically is not used to measure drug concentration. In one example, the system electronics for controlling breath sample may use this information and expose the sensors to the end tidal breath for measuring concentration of various components of breath sample. In another example the sensor electronics comprises modified drug sensor, which is constantly monitoring the drug concentration in breath. The system electronics may extract the right concentration measurement at the same time when the $CO_2$ sensor detects the end tidal breath. Similarly, an $O_2$ sensor may be used for the same purpose as of $CO_2$ sensor. The $CO_2$ sensor may also be used to provide real time monitoring of respiration condition of the patient undergoing anesthesia or other procedures. In cases of abnormal $CO_2$ concentration, typically an alarm is triggered to alert the doctor or other individuals associated with the anesthesia procedure.

In accordance with one embodiment, the gas sensor is used to detect the concentration of anesthetic drug from exhaled breath of patients during general and total intravenous anesthesia procedure. Measuring concentration of the anesthetic drug in the breath sample is performed using every breath sample or an average of several breath samples. The sensor reading is proportional to the concentration of the anesthetic drug in the breath sample. In one embodiment, the gas sensor measures the vapor concentration of intravenously delivered drug in the patient's exhaled breath. The gas sensor measurement is performed continuously or every few minutes. In one or more examples, the drug vapor sensor detects anesthetic drug, such as propofol in a patient's breath sample. The calculated anesthetic drug concentration in plasma may trigger an alarm if the value is higher than a preset threshold value. A typical concentration of propofol in the breath of a patient undergoing intravenous anesthesia using propofol is, for example, from 0 ppb to 20 ppb. To measure an accurate amount of drug in the breath sample, the sensors are required to be highly sensitive and selective. The detection limit of the sensor may be in the range of 0.1 ppb to 100 ppb, and the sensor needs to detect the concentration of drug without response to all other potential gas compounds in the breath, for example, acetone, ethanol, isoprene, ammonia, methanol, pentane, or ethane.

Typically, the drug concentration in plasma during anesthesia procedure may be monitored in real time. By using the drug concentration in breath, the drug concentration in plasma may be determined accurately, for example using a transfer function. The concentration of drug in plasma may be determined by calculating, computing or correlating the value of drug concentration in plasma using the value of drug concentration in a breath sample and a transfer function. Then the drug concentration in plasma is derived from the anesthetic drug concentration in a breath sample with the use of an appropriate transfer function, which may vary among different situations and for different patients. For example, in one embodiment, the value of transfer function may be dependent on the temperature of a patient's body, breathing flow rate, exhaled $CO_2$ concentration, inhaled and exhaled oxygen concentration, age, gender, weight, height, BMI, or lung function parameters of a patient. The transfer function has an input and an output value. For example, the input of the transfer function may depend on the anesthetic drug concentration in breath and the value of transfer function. The calculated concentration of drug in plasma may be used in several ways. In one embodiment, the input value of the transfer function depends on at least a measured anesthetic drug concentration in the exhaled end tidal breath of a patient. The output value of the transfer function generates the concentration of the delivered drug in plasma. In some examples of the methods, the transfer function follows a linear equation or a non-linear equation. In some other examples, the transfer function follows the non-linear equation with a second order or higher order.

The measurement of drug concentration in plasma using a breath sample is in part based on the fact that the drug concentration in plasma may be correlated to the drug concentration in breath. This correlation is represented by a transfer function. To monitor plasma concentration of intravenously delivered drugs, a transfer function is used to calculate the plasma concentration. The input of the transfer function comprises at least measured drug concentration in the exhaled breath of the patient. The output of the transfer function is the plasma concentration of the delivered drug. Other potential inputs to the transfer function may also be used to improve the accuracy of the calculation, for example, exhaled end tidal carbon dioxide concentration, exhaled pressure and flow rate, patient body temperature, patient body weight, age, gender, weight, height, BMI, or lung function parameters of a patient. In some embodiments, the format of the transfer function may be linear with only first order terms. In some other embodiments, the format of the transfer function may be nonlinear with a second order or even higher order terms to achieve better calculation accuracy.

Parameters for an Example of Transfer Functions:

Plasma drug concentration: $C_p$; Breath drug concentration: $C_b$, Exhaled end tidal $CO_2$ concentration: $C_{co2}$, Breathing flow rate: $F_b$, Patient body weight: W, Patient body temperature: T

EXAMPLE 1

$$C_p = a \cdot C_b + b \quad \text{eq (1)}$$

In this example, the only input of the transfer function is $C_b$ on the right side of the equation. The output of the transfer function is the plasma concentration of the drug $C_p$ on the left side of the equation. "a" is a fitting parameter multiplied to $C_b$, and "b" is a fitting parameter to compensate for any offset between drug concentration in breath sample and drug concentration in plasma. The a and b are empirical numbers established from experiments, where the drug concentrations in breath sample are measured from patients. Linear regression fitting is used to extract the numerical value of fitting parameters a and b. Once a and b are established with enough statistical confidence, eq (1) may be used to predict plasma concentration of the target drug if the breath concentration of the drug is measured. Eq (1) is the simple transfer function with only first order terms. In real application, it provides the benefit of a simple numerical calculation, requiring less computing power and system memory to store fitting parameters.

EXAMPLE 2

$$C_p = a \cdot C_b + b \cdot C_b^2 + c \quad \text{eq (2)}$$

In this example, the input of the transfer is just the breath drug concentration $C_b$ on the right side of the equation. The output of the transfer function is the plasma concentration of the drug $C_p$ on the left side of the equation. a is a fitting parameter multiplied to $C_b$, b is the second order fitting parameter multiplied to the square of the breath drug concentration, and c is a fitting parameter to compensate for offset. The fitting parameters are established empirically. One difference between eq (2) and eq (1) is the addition of a second order term, which provides better prediction accuracy but typically requires more computing power and data storage space.

EXAMPLE 3

$$C_p = [(a \cdot C_b)/C_{co2}] + b \quad \text{eq (3)}$$

In this example, the inputs of the transfer function are the breath drug concentration $C_b$ and the exhaled end tidal carbon dioxide concentration $C_{CO2}$ on the right side of the equation. The output of the transfer function is the plasma concentration of the drug $C_p$ on the left side of the equation. a is a fitting parameter multiplied to the division product of the breath drug concentration to the end tidal carbon dioxide concentration. b is a fitting parameter to compensate for offset. Both a and b are empirical fitting parameters extracted from measured plasma drug concentration, breath drug concentration and end tidal carbon dioxide concentration. Once fitting parameters a and b are established with enough statistical confidence, eq (3) may be used to predict plasma drug concentration with the input of measured breath drug concentration and end tidal carbon dioxide concentration. In this transfer function, end tidal carbon dioxide concentration is used to normalize measured breath drug concentration. Normalization reduces the prediction error between different patients from their different respiration condition. Patients with higher end tidal carbon dioxide concentration may have better gas exchange efficiency and therefore higher exhaled drug concentration with the same delivered dosage with a patient with lower exhaled carbon dioxide concentration. Another benefit of using carbon dioxide concentration is that, if there is any dilution effect from the sampling or measurement process, the same dilution effect may occur with carbon dioxide concentration as well. Therefore, using carbon dioxide concentration to normalize the drug concentration reduces the measurement variation due to these effects.

For example, propofol with same dosage is intravenously delivered to two patients having identical weight. One patient has a higher end tidal exhaled carbon dioxide concentration around 5%. The other patient has a low end tidal carbon dioxide concentration around 4.5%. This means the first patient has better gas exchange efficiency in his lung than the second patient. Although their plasma drug concentrations are the same, their exhaled drug concentration may be different due to their lung gas exchanging difference. With the same plasma concentration, the first patient may have a 10% higher breath drug concentration than the second patient. Therefore, by using eq (1) to predict plasma concentration, there is a 10% difference between the two patients. This shows that eq (1) does not give accurate plasma concentration values if there is variation in patient's lung gas exchange rate. However, using exhaled carbon dioxide concentration to normalize the breath drug concentration to predict plasma concentration using eq (3), the error can be eliminated.

EXAMPLE 4

$$C_p = [(a \cdot C_b)/(b \cdot C_{co2} + c \cdot F_b)] + d \qquad \text{eq (4)}$$

In this example, patient breathing flow rate is also used as an input to the transfer function. Sensing technologies that are used to measure gas concentration are typically flow rate dependent. Adding flow rate as an input to the transfer function may reduce measurement variation introduced from breathing flow rate variations. Eq(4) is just one example showing how flow rate may be incorporated in the transfer function. Flow rate may also be incorporated in other ways.

EXAMPLE 5

$$C_p = a \cdot C_b/W + b \qquad \text{eq (5)}$$

In this example, patient body weight is used as an input to the transfer function. Body weight is used in pharmacokinetic models to calculate the right drug dosage in many intravenous drug delivery practices. For example, recommended dosage for propofol is: for initial Bolus: 0.8-1.2 mg/kg; for infusion: start at 140-200 µg/kg/min, at 10 min: 100-140 µg/kg/min, after 2 hours: 80-120 µg/kg/min. Body weight is proportional to the blood volume of a patient. Therefore, it is also often an important parameter for drug concentration in blood or plasma and the drug concentration in breath sample. Using patient body weight as an input parameter may potentially normalize prediction error from body weight variation of different patients.

EXAMPLE 6

$$C_p = a \cdot C_b \cdot e^{(T/T0)\beta} + b \qquad \text{eq (6)}$$

In this example, patient body temperature is used as an input to the transfer function. The volatility of a drug compound is dependent on the body temperature. The higher the body temperature, the higher is the breath drug concentration. By incorporating body temperature into the transfer function, eq (6) may reduce temperature variation that causes prediction error of plasma drug concentration.

The given examples are non-limiting examples of potential transfer functions that may be used to calculate drug concentration in plasma based on measured values of drug concentration in breath, end tidal carbon dioxide concentration, breathing flow rate, body weight, or body temperature. Other transfer functions may be formed by using given transfer function examples to incorporate all or a sub set of these inputs. Additional inputs may be included. These inputs may be the physiological conditions of the patient, environmental parameters or measurement system and components related parameters, among others.

One or more other examples may be used to obtain accurate end-tidal propofol values. By adding a $CO_2$ sensor to the mixing chamber in which the mixed propofol concentration is measured, the end-tidal concentration of propofol may easily and accurately be solved. In the following, Cx is the mixed expired concentration measured in the mixing chamber, cx(t) is the expired concentration as a function of time, and $c^{et}x$ is the end-tidal concentration of either x=propofol or x=$CO_2$. $V_{mixed}$ is the volume of the mixing chamber and f(t) is the expired flow as a function of time. Sampling for the mixing chamber can be done either from the D-lite (on common sampling point) or from the expiratory limb of the breathing circuit (two sampling points; one for the gas module and another for the mixing chamber). In both of these examples, $$\int_{exp} f(t) c_{CO2}(t) dt = a' \cdot V_{mixed} C_{CO2} \qquad \text{eq (7)}$$

$$\int_{exp} f(t) c_{PRO}(t) dt = a' \cdot V_{mixed} C_{PRO} \qquad \text{eq (8)}$$

where a' is a constant that depends on the sampling flow. The exhaled $CO_2$ and propofol curves are assumed to have the same shapes so that they differ only by a constant factor k. This is a feasible assumption if there is no propofol in the inhaled gas. This is typical at least in the intensive care unit (ICU) respirators with an open circuit; perhaps also in the anesthesia machines, where propofol gets absorbed. In this case:

$$c_{PRO}(t) = k \cdot c_{CO2}(t) \qquad \text{eq (9)}$$

and therefore also for the end-tidals $$c_{PRO}^{et} = k \cdot c_{CO2}^{et} \qquad \text{eq (10)}$$

From eqns. (7)-(9) for the mixed concentrations:

$$C_{PRO} = k \cdot C_{CO2} \qquad \text{eq (11)}$$

From eqns (10) and (11), a simple equation for the end-tidal propofol concentration is derived as:

$$c_{PRO}^{et} = \frac{C_{PRO} c_{CO2}^{et}}{C_{CO2}} \qquad \text{eq (12)}$$

The measurement of the concentrations of propofol and $CO_2$ in the mixing chamber, and the end-tidal $CO_2$ is significant, however in some cases accurate measurement of the flow may not require dependence on the user's need. The need to synchronize and integrate flow with the $CO_2$ concentration is avoided, a step that is prone to introduce errors.

The basic assumption for eqn. (9) is not valid, for example, if one of the two gases is more strongly absorbed in the airways or tubings, then it is not possible to correct for the deadspace. Therefore, the end-tidal portion of the expired propofol utilizing a valve is required to be processed for further detection. Controlling the valve for accurate measurement is desirable. The pressure and flow signals are not in synchrony with the gases; the measured $CO_2$ curve of the gas module is not in synchrony either. The time delays are not constants but rather depend on the dynamic pressure variations so synchronization may be somewhat cumbersome but not impossible.

The easiest solution might again be to add a second $CO_2$ sensor close to the opening valve of the mixing chamber and use this $CO_2$ signal to open and close the valve that lets in the end-tidal portion of the expired gas. This requires of course that this signal may be obtained and processed fast enough. Again, sampling may be done either from the D-lite or from the expiratory limb. One sampling point may be preferred with one gas module that handles all measurements.

In one or more examples, the method provides a safety alarm if the concentration of anesthetic drug is higher than a safety threshold value preset by the anesthesiologist. The "safety threshold value" means a threshold value of the anesthetic drug concentration which is safe for the patient undergoing anesthesia procedure. In some examples of the method, the monitoring of anesthetic drug concentration in plasma is a continuous real time process. In this example, the real time anesthetic drug concentration in plasma helps the anesthesiologist to adjust the drug dosage.

To determine a dosage regimen for an anesthetic drug delivered to a patient is significant for delivery rate of the drug to achieve a desired pharmacologic effect for the patient while any associated side effects are minimized. Some of the anesthetic drugs have a close relationship between their dosage regimen, for example propofol, remifentanil, and afentanil. The administration of the drug based on the dosage regimen on the pharmacokinetic model may be improved. In another example, the concentration of drug in plasma may be used in conjunction with a pharmacokinetic model to provide correction to the pharmacokinetic predication of anesthetic drug concentration in plasma. Using a computer with a pharmacokinetic program permits control of a desired plasma concentration of an agent, such as propofol. Target controlled infusion is one of the methods for administering an intravenous anesthesia agent using a computer to control the infusion pump.

In one or more examples, the methods for monitoring a propofol concentration in plasma, comprise forming a breath sample using a patient's breath, exposing one or more sensors to the breath sample, detecting the propofol in the breath sample, measuring a concentration of propofol in the breath sample, and determining a concentration of the propofol in a plasma of the patient using a transfer function and the concentration of the propofol in the breath sample. The sensors comprise at least one sensor for measuring propofol concentration and at least one sensor for measuring other gases. The sensors measure the concentration of propofol and the concentration of at least another gas in the breath sample.

In some examples, the methods provide a more accurate measurement of anesthetic drug concentration, such as propofol in plasma than pharmacokinetic models. Using a multi-parameter transfer function is a more accurate and robust method than other breath based measurements. The method only uses the concentration of components or drugs in a breath sample as an input parameter to calculate a concentration of drug in plasma.

In some embodiments, the breath sample comprises end-tidal gas, gas from dead-space, inspiratory gas, or combinations thereof. The propofol concentration in the breath sample comprises mixed gases, such as combination of end-tidal gas, gas from dead-space, and inspiratory gas, is easier using available sensors. The propofol concentration in the end tidal gas is determined by determining the concentration of another gas in the end tidal gas, and also by assuming a ratio of the concentration of propofol and another gas in the end-tidal gas and the ratio of the concentration of propofol and another gas in the breath sample comprises mixed gases are same. For example, the end-tidal concentration of propofol measurement may be difficult because of unavailability of a fast sensor that may measure the very low concentration of propofol in end tidal gas. Instead, the concentrations of propofol and another gas in the mixed gas sample is easily measurable. The measurement of the end-tidal concentration of another gas, such as $CO_2$ may be easier as fast 10ms sensors are available. The end tidal concentration of propofol may be determined by making an assumption of equal ratios of propofol and $CO_2$ in mixed gases and in the end tidal gas as described above. Therefore, the plasma concentration of propofol is determined using the propofol concentration in the end-tidal gas using the above method and assumption.

As illustrated in FIG. 1, a flow chart for the method of intravenous drug monitoring is provided that includes various consecutive steps. The anesthesia monitoring process starts with determining an intravenous drug dosage required for a particular application for a patient. An anesthetic drug is intravenously administered to the patient according to the determined drug dosage for a specific application. An inhaled and exhaled breath sample is collected from the patient to sample the breath. The drug vapor concentration of the anesthetic drug is measured using a patient's breath. The concentration of the drug in plasma of the patient is determined using a transfer function and the concentration of the component in the breath sample. The parameters for transfer function may include, but are not limited to, the value of transfer function and may be dependent on the temperature of a patient's body, breathing flow rate, exhaled $CO_2$ concentration, inhaled and exhaled oxygen concentration, age, gender, weight, height, BMI, or lung function parameters of a patient. The concentration of the drug in the plasma is then compared with a target value. An alarm is triggered if the calculated concentration of the anesthetic drug in plasma is higher than the target value. If the value is within a target range, the procedure is repeated again starting from delivery of intravenous drug, as per the requirement of the procedure or user need. If a value of calculated drug concentration is out of the range of the target value, the procedure may be repeated starting, for example, from determination of the drug dosage.

The following examples are intended to be illustrative of suitable methods, which are not the only methods suitable for use in the various aspects and embodiments of the invention and should not be viewed as limiting the scope of the invention.

Experiment 1—Detection Limit of Bare Glassy Carbon (GC) Electrode

Figure 2A:
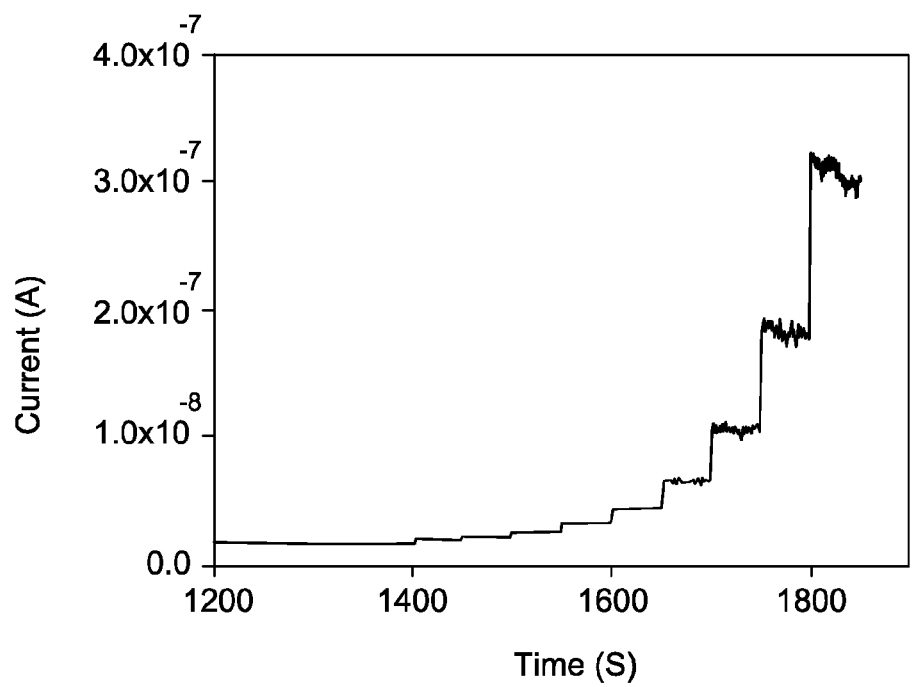
FIG. 2A is a graph of amperometric results of propofol on a bare glass carbon (GC) electrode at 0.51V.

Electro-generated oligomers prefer to diffuse away from electrode surfaces instead of depositing on surfaces when their concentration is very low (<1 mM). Since the targeted propofol concentration is at ppb levels, it is worth deciding the minimum concentration of propofol to foul the bare electrode. The current response of propofol in pH 7 buffer was shown in FIG. 2A with oxidation potential set at 0.51V. It was found that the bare glassy carbon (GC) electrode does not have fouling issues at propofol concentration lower than 1 ppm, which was verified by their stable current response over scanning time (FIG. 2A). When propofol concentration is larger than 1ppm, current dropped with time and the intensity was not stable any more (FIG. 2A).

Figure 2B:
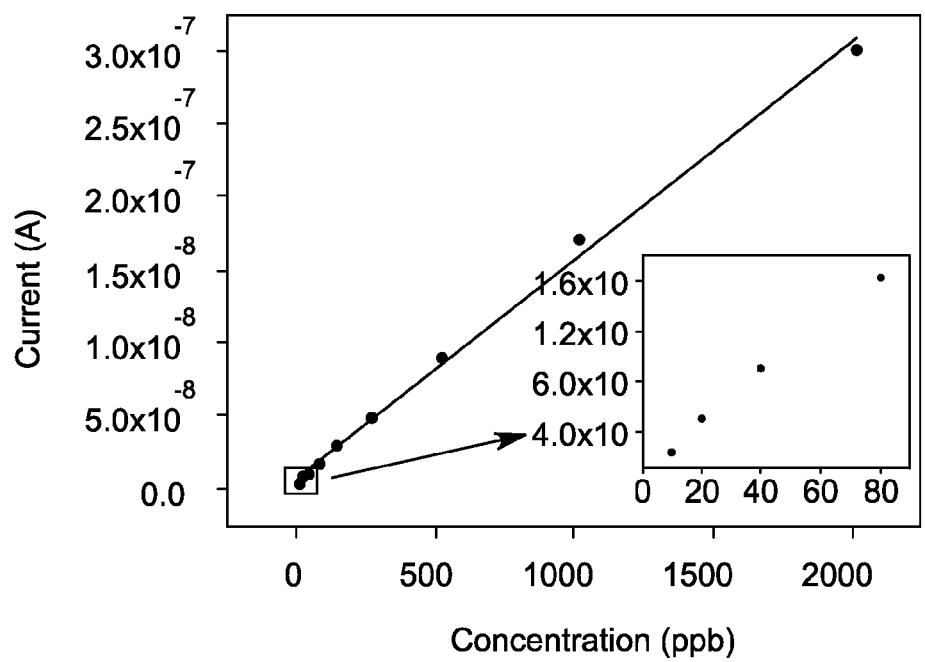
FIG. 2B is a graph of a scatter plot of current versus propofol concentration for a bare GC electrode.

FIG. 2B displays the calibration curve between propofol concentration and current intensity. 10 ppb propofol sample produced clear signal and the limit of detection was determined as 1 ppb based on the same criterion described before. All points in the 10-80 ppb ranges are displayed as inset for clarity. The red line is the regression curve of all data points with a transfer function Ipropofol (nA)=0.15*Cpropofol (ppb)+5.96 ($R^2$=0.996, fitted concentration range 10 ppb to 2000 ppb). The large linear response range (from 10 ppb to 2000 ppb) ensures a large operation window for its applications.

The scope of the invention is defined by the claims, and may comprise other examples not specifically described that would occur to those skilled in the art. Such other examples are intended to be within the scope of the claims.

The invention claimed is:

1. A non-invasive method of monitoring an anesthetic drug concentration in plasma of a patient using the patient's breath, comprising:
   (a) administering an anesthetic drug to the patient using an infusion pump;
   (b) collecting a breath sample using a breathing circuit connected to the patient, wherein the breath sample comprises a mixed gas comprising a combination of end-tidal gas, gas from dead-space, and inspiratory gas;

(c) exposing a system comprising a detector, a processor, and one or more sensors to the breath sample;

(d) detecting one or more components of the anesthetic drug in the breath sample using the detector;

(e) measuring a concentration of at least one of the one or more components of the anesthetic drug in the breath sample using the one or more sensors;

(f) measuring one or more parameters of the patient using the one or more sensors; and (g) determining an anesthetic drug concentration in plasma of the patient based on the measured concentration of the at least one of the one or more components of the anesthetic drug in the breath sample and the one or more parameters of the patient using the processor, wherein the processor is configured to calculate the anesthetic drug concentration using a transfer function, and wherein the anesthetic drug concentration is a concentration of the one or more components of the anesthetic drug in the plasma of the patient; wherein the transfer function comprises an input value and an output value, wherein the transfer function comprises a non-linear equation that uses a second order or a higher order, and wherein the input value of the transfer function at least depends on a temperature parameter of the one or more parameters to normalize the measured concentration in the breath sample;

(h) providing a target range of the anesthetic drug concentration;

(i) comparing the anesthetic drug concentration with the target range;

(j) if the anesthetic drug concentration is outside the target range:
  (1) generating an alarm;
  (2) adjusting an anesthetic drug dosage to the patient;
  (3) delivering the anesthetic drug to the patient; or (k) if the anesthetic drug concentration is within the target range:
  (1) delivering the anesthetic drug to the patient; and (l) repeating steps (b) through (k) as needed until procedure is completed.

2. The method of claim 1, wherein collecting the breath sample comprises use of two or more of filtration, concentration, differential permeation, dilution, desiccation, breath pressure control, breath temperature control, breath humidity control, breath flow rate control, or vapor density normalizing techniques.

3. The method of claim 1, wherein collecting the breath sample is performed periodically or continuously.

4. The method of claim 1, wherein the sensors are selected from two or more of pressure sensors, temperature sensors, flow rate sensors, humidity sensors, gas sensors, or drug vapor sensors.

5. The method of claim 4, wherein the drug vapor sensors detect propofol in the breath sample.

6. The method of claim 1, wherein at least one of the components of the anesthetic drug is propofol.

7. The method of claim 1, wherein measuring the concentration of the at least one of the one or more components of the anesthetic drug in the breath sample is performed using every breath sample or an average of several breath samples over a determined period of time.

8. The method of claim 1, wherein the input value of the transfer function depends on the anesthetic drug concentration in exhaled end tidal breath, carbon dioxide concentration in exhaled end tidal breath, pressure of exhaled breath, flow rate of exhaled breath, patient's body weight, patient's gender, age of the patient, body mass index (BMI) of the patient, lung function of the patient, or combinations thereof.

9. The method of claim 8, wherein the input value of the transfer function depends on at least the measured anesthetic drug concentration in exhaled end tidal breath of the patient.

10. The method of claim 1, wherein the method is a continuous real time process.

11. A non-invasive method of monitoring a propofol concentration in a plasma of a patient, comprising:

(a) administering an anesthetic drug comprising propofol to the patient using an infusion pump;

(b) collecting a breath sample using a breathing circuit connected to the patient, wherein the breath sample comprises a mixed gas comprising a combination of end-tidal gas, gas from dead-space, and inspiratory gas;

(c) exposing a system comprising a detector, a processor, and one or more sensors to the breath sample;

(d) detecting propofol in the breath sample using the detector;

(e) measuring a concentration of propofol in the breath sample using the one or more sensors;

(f) measuring one or more parameters of the patient using the one or more sensors; and (g) determining a propofol concentration in plasma of the patient based on the measured concentration of propofol in the breath sample and the one or more parameters of the patient using the processor, wherein the processor is configured to calculate the propofol concentration using a transfer function and the concentration of the propofol in the breath sample, wherein the transfer function comprises an input value and an output value, and wherein the transfer function comprises a non-linear equation that uses a second order or higher order, and the input value of the transfer function at least depends on a temperature parameter of the one or more parameters to normalize the measured breath drug concentration;

(h) providing a target range of propofol in the plasma of the patient;

(i) comparing the propofol concentration with the target range;

(j) if the propofol concentration is outside the target range:
  (1) generating an alarm;
  (2) adjusting a propofol dosage to the patient;
  (3) delivering the anesthetic drug comprising propofol to the patient; or (k) if the propofol concentration is within the target range:
  (1) delivering the anesthetic drug comprising propofol to the patient; and (l) repeating steps (b) through (k) as needed until procedure is completed.

12. The method of claim 11, wherein the transfer function depends on the propofol concentration in exhaled end tidal breath, carbon dioxide concentration in exhaled end tidal breath, pressure of exhaled breath, flow rate of exhaled breath, patient's body weight, patient's gender, age of a patient, body mass index (BMI) of a patient, lung function of the patient, and combinations thereof.

13. The method of claim 11, wherein the sensors comprise at least one sensor for measuring the concentration of propofol and at least one sensor for measuring other gases in the breath sample.

14. The method of claim 13, wherein the sensors measure the concentration of propofol and a concentration of at least another gas in the breath sample.

15. The method of claim 14, wherein the propofol concentration is determined by determining the concentration of the at least another gas in the end tidal gas and assuming a ratio of the concentration of propofol and another gas in the end-tidal gas and the ratio of the concentration of propofol and the at least another gas in the breath sample are same.

16. The method of claim 15, wherein the propofol concentration is determined using the propofol concentration in the end-tidal gas.

\* \* \* \* \*